United States Patent
Suh et al.

(10) Patent No.: US 10,130,397 B2
(45) Date of Patent: Nov. 20, 2018

(54) ORTHOPEDIC FASTENER BLOCKING SYSTEM

(71) Applicant: GLOBUS MEDICAL, INC, Audubon, PA (US)

(72) Inventors: Sean Suh, Plymouth Meeting, PA (US); Mark Weiman, Coatesville, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 231 days.

(21) Appl. No.: 14/206,460

(22) Filed: Mar. 12, 2014

(65) Prior Publication Data
US 2014/0194929 A1 Jul. 10, 2014

Related U.S. Application Data

(63) Continuation of application No. 12/433,255, filed on Apr. 30, 2009, now Pat. No. 8,709,053.

(51) Int. Cl.
*A61B 17/80* (2006.01)
*A61B 17/70* (2006.01)
*A61B 17/86* (2006.01)

(52) U.S. Cl.
CPC .......... *A61B 17/7049* (2013.01); *A61B 17/86* (2013.01)

(58) Field of Classification Search
CPC ............ A61B 17/8033; A61B 17/8042; A61B 2017/8655; A61B 17/844; A61B 17/846
See application file for complete search history.

(56) References Cited

U.S. PATENT DOCUMENTS

| 2,685,877 | A | * | 8/1954 | Dobelle | A61F 2/3603 411/21 |
|---|---|---|---|---|---|
| 5,364,399 | A | * | 11/1994 | Lowery | A61B 17/1728 606/286 |
| 2007/0093838 | A1 | * | 4/2007 | Khodadadyan-Klostermann | A61B 17/7059 606/70 |
| 2008/0281326 | A1 | * | 11/2008 | Watanabe | A61B 17/164 606/62 |
| 2010/0145397 | A1 | * | 6/2010 | Overes | A61B 17/68 606/319 |

* cited by examiner

*Primary Examiner* — Olivia C Chang

(57) ABSTRACT

In an exemplary embodiment, the present invention provides an orthopedic fastener blocking system that allows for a desirable number of fasteners to be used with an orthopedic device even when the orthopedic device is too small to accommodate a desired number of traditionally located and oriented fasteners or when the accessibility to the device is reduced so that addressing a desired number of traditionally located and oriented fasteners is not possible. The system includes an orthopedic implant and at least first and second fasteners where one of the first and second fasteners prevents the other of the first and second fasteners from uninstalling when the first and second fasteners are in the installed position.

7 Claims, 1 Drawing Sheet

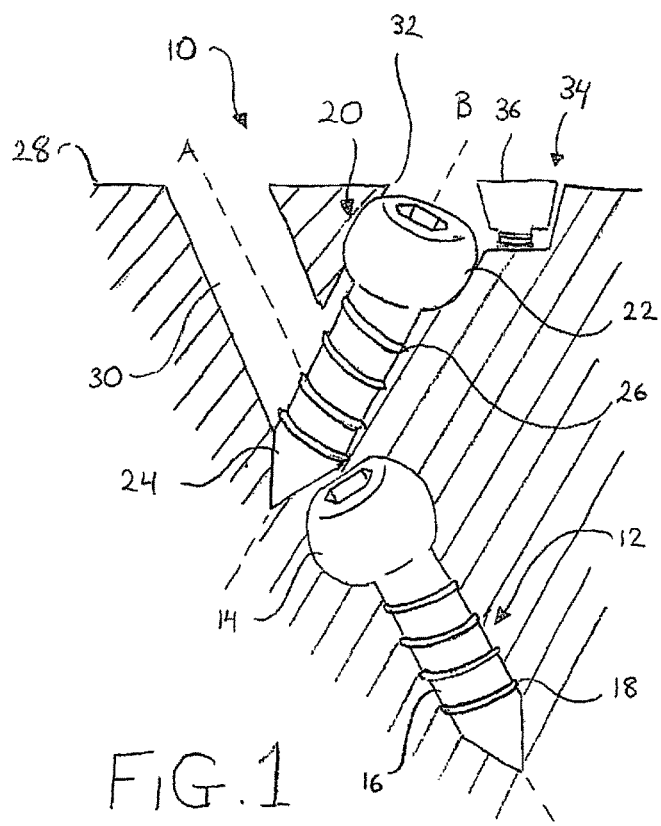
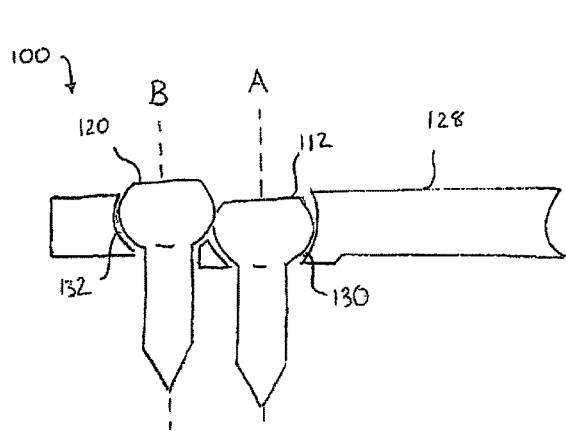
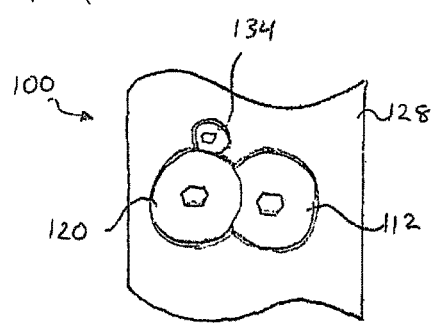
FIG. 1
FIG. 2
FIG. 3

ORTHOPEDIC FASTENER BLOCKING SYSTEM

CROSS-REFERENCE TO RELATED APPLICATIONS

This application is a continuation application of U.S. patent application Ser. No. 12/433,255 filed on Apr. 30, 2009, which is incorporated in its entirety herein.

FIELD OF THE INVENTION

The present invention is generally directed to orthopedic fasteners used to secure an orthopedic device to bone tissue. In particular, the present invention relates to a system of blocking the orthopedic fasteners to prevent the fasteners from disengaging or dislodging from the orthopedic implant.

BACKGROUND OF THE INVENTION

As is known in the field of orthopedic surgery, and more specifically spinal surgery, orthopedic fasteners may be used for fixation or for the anchoring of orthopedic devices or implants to bone tissue. An exemplary use of orthopedic fasteners can include using the fasteners to fasten an orthopedic device or implant, such as a bone plate, a spinal rod, or a spinal spacer to a vertebral body for the treatment of a deformity or defect in a patient's spine. Focusing on the bone plate example, orthopedic fasteners can be secured to a number of vertebral bodies and a bone plate can then be connected to the vertebral bodies via the orthopedic fasteners to fuse a segment of the spine. Turning to the spinal spacer example, orthopedic fasteners can be used to fix the location of a spinal spacer once the spacer is implanted between adjacent vertebral bodies. In each of the examples, orthopedic fasteners are used in conjunction with the orthopedic implant to treat the affected area.

However, in some cases, where the size of the treatment area requires a smaller implant or the location of the area needed to be treated dictates reduced accessibility, the number and location of the fasteners may be limited. With a reduced number of fasteners, it is possible that the orthopedic device can become dislodged or disconnected from the area of treatment.

In addition, over time, it has been found that as a result of the forces placed upon the orthopedic device and fasteners resulting from the movement of the spine, the orthopedic fasteners can begin to "back out" from their installed position eventually resulting in the fasteners disconnecting from the device.

As such, there exists a need for an orthopedic fastener blocking system that allows for a desirable number of fasteners to be used with an orthopedic device regardless of the device size and accessibility where the fasteners are blocked to prevent the fasteners from "backing out" of their installed position.

SUMMARY OF THE INVENTION

In one embodiment, the present invention provides an orthopedic fastener blocking system that allows for a desirable number of fasteners to be used with an orthopedic device even when the orthopedic device is too small to accommodate a desired number of traditionally located and oriented fasteners or when the accessibility to the device is reduced so that addressing a desired number of traditionally located and oriented fasteners is not possible. The system, in one embodiment, includes an orthopedic implant and at least first and second fasteners where one of the first and second fasteners prevents the other of the first and second fasteners from uninstalling when the first and second fasteners are in the installed position.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a partial perspective view of one embodiment of an orthopedic fastener blocking system;

FIG. 2 is a schematic side view of another embodiment of an orthopedic fastener blocking system; and FIG. 3 is schematic top view of the system shown in FIG. 2;

DETAILED DESCRIPTION OF THE PREFERRED EMBODIMENTS

The following description of the preferred embodiment(s) is merely exemplary in nature and is in no way intended to limit the invention, its application, or uses.

With reference to FIG. 1, an embodiment of an orthopedic fastener blocking system 10 is illustrated. Although the system 10 is shown isolated from the environment it would typically be used in, it should be understood that the system 10 provides a fastening and fastener blocking system that allows for a desirable number of fasteners to be used with an orthopedic device when the orthopedic device is too small to accommodate a desired number of traditionally located and oriented fasteners or when the accessibility to the device is reduced so that addressing a desired number of traditionally located and oriented fasteners is not possible.

The system 10 preferably includes an orthopedic device or implant 28; at least a first fastener 12 having a head portion 14, a shank portion 16, and threads 18 that surround at least a portion of the shank portion 16; and a second fastener 20 having a head portion 22, a shank portion 24, and threads 26 that surround at least a portion of the shank portion 24. Although only two fasteners are shown, it is contemplated that the system 10 can include any number of fasteners. Further, the implant 28 can be any one of a number of spinal implants including bone plates, spinal rods, and intervertebral spacers.

The system 10 can also include a blocking mechanism 34 which, in one embodiment, is a set screw having an enlarged head portion 36. Although the blocking mechanism 34 is identified as being a set screw, any mechanism that would serve as a blocking mechanism is contemplated, such as a cam type mechanism or a slideable interference mechanism. Alternatively, a separate blocking mechanism may not be included at all, rather a channel in the implant 28 may be configured and dimensioned to allow a fastener to pass through in one direction put prevent the fastener from moving in the opposite direction.

With continued reference to the embodiment of the system 10 shown in FIG. 1, the implant 28 includes channels 30 and 32, the channels 30 and 32 being configured and dimensioned to receive the fasteners 12 and 20. The channels 30 and 32 each have a separate and spaced opening and each define a longitudinal axis, axis A and axis B, respectively. In one embodiment, longitudinal axis A and longitudinal axis B intersect at a non-perpendicular, and preferably acute, angle. As further explained below, this intersecting configuration allows for the blocking of one fastener by a second fastener and allows for the placement of the fasteners in closer proximity to each other. It should be noted that although only two channels are discussed, it is contemplated that the implant 28 can include any number of channels and each channel is capable of receiving at least one fastener.

In an exemplary use of the system 10 as shown in FIG. 1, the implant 28 is placed on or near the area of treatment. The fastener 12 is installed through channel 30 along axis A from a first uninstalled position to a second installed position where the fastener 12, in the installed position, engages the implant 28 as well as the anatomy in the area of treatment to secure implant 28 in place. After the fastener 12 is installed in place, the fastener 20 is installed through channel 32 along axis B from a first uninstalled position to a second installed position. The orientation of channels 30 and 32 and axes A and B are such that when the fastener 20 is installed, it will intersect the path of installation of fastener 12. Accordingly, the fastener 20, when in the second installed position, engages the implant 28 and the anatomy of the area of treatment as well as blocks fastener 12 from "backing out" or from moving in an opposite direction from the direction of installation. More specifically, the fastener 20 can be installed in any number of positions along axis B and any portion of fastener 20 can be used to block the fastener 12 including the head portion 22 or the shaft portion 24. Once the fastener 20 is installed in place, the blocking mechanism 34 is manipulated so that the enlarged head portion 36 blocks fastener 20 from "backing out" or from moving in an opposite direction from the direction of installation.

Turning to FIGS. 2 and 3, another embodiment of an orthopedic fastener blocking system 100 is shown. The system 100 preferably includes at least a first fastener 112, a second fastener 120, and an orthopedic implant 128. Although only two fasteners are shown, it is contemplated that the system 100 can include any number of fasteners. Further, the implant 128 can be any one of a number of spinal implants including bone plates, spinal rods, and intervertebral spacers.

The system 100 can also include a blocking mechanism 134. Alternatively, a separate blocking mechanism may not be included at all, rather a channel in the implant 128 may be configured and dimensioned to allow a fastener to pass through in one direction put prevent the fastener from moving in the opposite direction.

With continued reference to the embodiment of the system 100 shown in FIGS. 2 and 3, the implant 128 includes channels 130 and 132, the channels 130 and 132 define a longitudinal axis, axis A and axis B, respectively, and are configured and dimensioned to receive the fasteners 112 and 120. In one embodiment, the openings of the channels 130 and 132 each have intersecting openings and longitudinal axes A and B are generally parallel to each other. As further explained below, this channel configuration allows for the blocking of one fastener by a second fastener. It should be noted that although only two channels are discussed, it is contemplated that the implant 128 can include any number of channels and each channel is capable of receiving at least one fastener.

In an exemplary use of the system 100 as shown in FIGS. 2 and 3, the implant 128 is placed in the area of treatment. The fastener 112 is installed through channel 130 along axis A from a first uninstalled position to a second installed position where the fastener 12, in the installed position, engages the implant 28 as well as the anatomy in the area of treatment to secure implant 28 in place. After the fastener 112 is installed in place, the fastener 120 is installed through channel 132 along axis B from a first uninstalled position to a second installed position. The intersection of channels 130 and 132 is such that when the fastener 120 is installed, it will intersect the path of installation of fastener 112. Accordingly, the fastener 120, when in the second installed position, engages the implant 128 and the anatomy of the area of treatment as well as blocks fastener 112 from "backing out" or from moving in an opposite direction from the direction of installation. More specifically, the fastener 120 can be installed in any number of positions along axis B and the head portion of the fastener 120 can be used to block the fastener 112. Once the fastener 120 is installed in place, the blocking mechanism 134 is manipulated so that a portion of the blocking mechanism 134 blocks the fastener 120 from "backing out" or from moving in an opposite direction from the direction of installation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A fastening assembly for fastening an orthopedic implant to bone tissue, comprising:

an orthopedic implant having a blocking mechanism and at least a first channel and a second channel, the first channel defining a first longitudinal axis and the second channel defining a second longitudinal axis, wherein the orthopedic implant has an upper surface and a lower surface, and wherein the first channel and the second channel are elongated in structure traversing through the orthopedic implant;

a first fastener comprising a shank portion having threads, the first fastener capable of being received in the first channel along the first longitudinal axis in a first direction from a first position to a second position; and a second fastener comprising a shank portion having threads, the second fastener capable of being received in the second channel along the second longitudinal axis in a second direction from a first position to a second position, wherein the first fastener and the second fastener are separate elements;

wherein a portion of the second fastener prevents the first fastener from moving in a direction opposite the first direction when the first fastener and the second fastener are in their respective second positions, wherein the first longitudinal axis of the first channel and the second longitudinal axis of the second channel intersect within a body of the orthopedic implant, and wherein the blocking mechanism is received in the upper surface of the orthopedic implant, wherein the first channel and the second channel are at an oblique angle with respect to one another.

2. The assembly of claim 1, wherein an opening to the first channel is separate and distinct from an opening to the second channel.

3. The assembly of claim 1, wherein the blocking mechanism blocks the second fastener from moving in a direction opposite the second direction.

4. The fastening assembly of claim 1, wherein the blocking mechanism is not coupled to the first fastener or the second fastener.

5. A fastening assembly for fastening an orthopedic implant to bone tissue, comprising:
- an orthopedic implant having a blocking mechanism and at least a first channel and a second channel, the first channel defining a first longitudinal axis and the second channel defining a second longitudinal axis, wherein the orthopedic implant has an upper surface and a lower surface, and wherein the first channel and the second channel are elongated in structure traversing through the orthopedic implant;
- a first fastener comprising a shank portion having threads, the first fastener received in the first channel along the first longitudinal axis in a first direction from a first position to a second position; and
- a second fastener comprising a shank portion having threads, the second fastener received in the second channel along the second longitudinal axis in a second direction from a first position to a second position, wherein the first fastener and the second fastener are are separate elements,
- wherein a portion of the second fastener prevents the first fastener from moving in a direction opposite the first direction when the first fastener and the second fastener are in their respective second positions,
- wherein the first longitudinal axis of the first channel and the second longitudinal axis of the second channel intersect within a body of the orthopedic implant, and
- wherein the blocking mechanism is received in the upper surface of the orthopedic implant,
- wherein the first channel and the second channel are at an oblique angle with respect to one another.

6. The fastening assembly of claim 5, wherein the first fastener and the second fastener are at different heights with respect to the upper surface and lower surface of the orthopedic implant in their respective second positions.

7. The fastening assembly of claim 5, wherein the blocking mechanism is not coupled to the first fastener or the second fastener.

* * * * *